United States Patent [19]

Erickson

[11] Patent Number: 4,500,585
[45] Date of Patent: Feb. 19, 1985

[54] CREPED ABSORBENT COMPOSITES

[75] Inventor: Robert E. Erickson, Midland, Mich.

[73] Assignee: The Dow Chemical Company, Midland, Mich.

[21] Appl. No.: 373,930

[22] Filed: May 3, 1982

[51] Int. Cl.³ .......................... B32B 3/28; B32B 27/10
[52] U.S. Cl. .................................. 428/152; 162/111;
428/153; 428/154; 428/246; 428/286;
428/308.4; 604/367; 604/378
[58] Field of Search ............... 428/152, 153, 154, 246,
428/286, 304.4, 308.4, 245; 162/111, 112;
264/282, 283; 604/358, 367, 372, 378

[56] References Cited

U.S. PATENT DOCUMENTS

| | | | |
|---|---|---|---|
| 4,093,765 | 6/1978 | Schmidt | 428/152 |
| 4,117,184 | 9/1978 | Erickson et al. | 428/224 |
| 4,260,443 | 4/1981 | Lindsay et al. | 428/198 |

FOREIGN PATENT DOCUMENTS 2375985  7/1978  France

*Primary Examiner*—Paul J. Thibodeau
*Attorney, Agent, or Firm*—B. G. Colley

[57] ABSTRACT

Creped absorbent composites made from lightly cross-linked or water-swellable hydrophilic polymers with layers of wicking substrates are disclosed. The creped composites are made by drying the composites to less than 8% moisture and creping them in a creping zone. The creped composites have a tissue-like feel at low relative humidities with rapid absorption and are useful to make low bulk, high fluid capacity personal care products. Absorbent pads made from the above composites are also disclosed wherein the pads comprise one or more layers of wicking substrates, a water impermeable bottom sheet, and a water permeable face sheet.

17 Claims, 2 Drawing Figures

CREPED ABSORBENT COMPOSITES

BACKGROUND OF THE INVENTION

This invention relates to creped absorbent composites wherein a lightly crosslinked or water-swellable hydrophilic polymer is bonded to wicking substrates, dried, and creped to give the composite a soft hand and high water absorption rates.

It is known from French Pat. No. 2,375,985 dated 9-1-78 that non-woven fiber sheet/wadding/powdered layer/wadding/polyethylene film laminates can be made flexible with good adhesion by transverse creasing or dry crimping. However, the present invention is superior in that there is a superior bonding and less migration of the absorbent material.

Another method of retaining powdered absorbents between sheets of cellulose tissue in small pockets is set forth in U.S. Pat. No. 4,260,443 dated 4-7-81. However, the product produced by this method is not as soft as the present invention.

In U.S. Pat. Nos. 4,117,184 and 4,176,667, it is disclosed that tissue/aerated absorbent film/tissue laminates can be prepared.

While the laminates disclosed in U.S. Pat. No. 4,117,184 have good absorption rates for water, urine, and other body fluids or exudates they have a tendency to become brittle and inflexible in atmospheres of low relative humidity. The result is an unacceptable rattle sound when the laminate is flexed and the laminate has a stiff or board like feel.

In U.S. Pat. No. 4,293,609, dated 10-6-81, there is disclosed a soft flexible hydrophilic absorbent laminate comprising a central discontinuous and crushed film made from a water-swellable hydrophilic polymer and layers of wicking substrates bonded to both sides of the film. However, the compositions of this invention are better in that they have a superior absorption rate.

SUMMARY OF THE INVENTION

It now has been found that creped composites comprising a layer containing a fractured and broken pieces of a water-swellable hydrophilic polymer combined with wicking substrates can be prepared which are both highly absorbent and flexible at low relative humidities.

The present invention is thus a creped hydrophilic absorbent composite which has a rapid absorption rate with a soft hand at low relative humidities which comprises the product produced by
 (a) reducing the moisture content of a composite of a water-swellable hydrophilic polymer with wicking substrates to less than 8% by weight by passing said composite through a drying zone, and
 (b) passing said dried composite through a creping zone wherein said polymer is fractured and broken into pieces which remain essentially laminated to said substrates.

A further aspect of the present invention is a method of making the above composites which comprises the steps of; reducing the moisture content of a composite of a lightly crosslinked hydrophilic polymer with wicking substrates to less than 8% by weight by passing said composite through a drying zone, if necessary, and passing said dried composite through a creping zone wherein said polymer is fractured and/or broken and which remains substantially adhered to said substrates.

The composites are useful to make absorbent articles such as baby diapers, adult diapers for incontinent patients, and the like since the composites and/or articles readily absorb aqueous solutions such as blood, urine, and other body exudates. The absorbent articles contain one or more layers of wicking substrates such as non-woven fiber mats, tissue wadding, or cellulose fluff together with a water impermeable bottom sheet such as polyethylene and a water permeable top sheet such as a non-woven fiber mat.

BRIEF DESCRIPTION OF THE DRAWING

The drawing is a photographic reproduction of one species of the present invention.

DETAILED DESCRIPTION OF THE INVENTION

Figure 1:
FIG. 1 shows a view taken with a scanning electron microscope of the absorbent composite with the top layer of paper tissue fibers pulled back to expose the broken or fractured film underneath. The bonding of the paper tissue fibers is clearly evident.
Figure 2:
FIG. 2 is an enlarged view of another example of the invention.

The water-swellable or lightly crosslinked hydrophilic polymers useful in this invention can be any of the known hydrophilic polymers that are capable of being formed into films, fibers or powders. Examples of such polymers are disclosed in U.S. Pat. Nos. 3,997,484; 3,926,891; 3,935,099; 4,090,013; and 4,190,562. These patents are incorporated by reference herein.

The preferred hydrophilic polymers useful in this invention are polyelectrolytes in the salt form. Examples of useful polyelectrolytes include ammonium or alkali metal salts of homopolymers of acrylic or methacrylic acid and copolymers with one or more ethylenically unsaturated comonomers.

Preferably the polyelectrolyte is a partially saponified polyacrylate polymer. The polymer before saponification is the result of reacting together a mixture of monomers which comprises (1) 30 to 92 percent by weight of an alkyl acrylate wherein the alkyl group has from 1 to 10 carbon atoms, an alkyl methacrylate wherein the alkyl group has from 4 to 10 carbon atoms, or mixtures thereof; (2) 8 to 70 percent by weight of an olefinically unsaturated carboxylic acid; and (3) 0 to 15 percent by weight of an omega hydroxyalkyl acrylate wherein the hydroxyalkyl groups has from 1 to 4 carbon atoms.

Examples of useful alkyl acrylates include methyl acrylate, ethyl acrylate, propyl acrylate, butyl acrylate, and hexyl acrylate. Examples of useful alkyl methacrylates include methyl methacrylate, ethyl methacrylate, hexyl methacrylate, octyl methacrylate and decyl methacrylate. Examples of useful omega hydroxyalkyl acrylates include 2-hydroxyethyl acrylate, hydroxymethyl acrylate, 3-hydroxypropyl acrylate and 4-hydroxybutyl acrylate.

The olefinically unsaturated carboxylic acids useful in this invention are mono or polycarboxylic acids. Examples of monocarboxylic acids include acrylic acid, methacrylic acid, crotonic acid, and isocrotonic acid. Examples of polycarboxylic acids include maleic acid, fumaric acid, and itaconic acid.

The foregoing polyacrylates are then dissolved in an aqueous alkali metal hydroxide solution. The amount of hydroxide solution employed is sufficient to saponify some of the acrylate esters to alkali metal carboxylates and to neutralize the carboxylic groups of the polyacrylate to alkali metal carboxylates so that the saponified polyacrylate polymer has from 30 to 70 weight percent alkali metal carboxylates.

The partially saponified polyacrylate polymer is employed as a solution containing from 5 to 60 percent by weight of the polymer.

A list of applicable polymers which could be prepared from readily available monomers and converted into their salt form is as follows:

acrylic acid—acrylate copolymers
acrylic acid—acrylamide copolymers
acrylic acid—olefinic copolymers polyacrylic acid
acrylic acid—vinyl aromatic copolymers
acrylic acid—styrene sulfonic acid copolymers
acrylic acid—vinyl ether copolymers
acrylic acid—vinyl acetate copolymers
acrylic acid—vinyl alcohol copolymers and
copolymers of methacrylic acid with all the above comonomers.

Illustrative examples of the polyfunctional crosslinking agents useful to convert the above polyelectrolytes into water-swellable polymers invention are set forth in U.S. Pat. Nos. 2,926,154; 3,224,986; and 3,332,901. These polyfunctional crosslinking agents are generally known as polyamide-polyamine epichlorohydrin adducts. The disclosures of these references are incorporated herein by reference. Similar crosslinking agents are also commercially available from Hercules Incorporated as Kymene 557 and Polycup 172. The structure of these adducts has been discussed in an article by M. E. Corr, et al Journal of Applied Polymer Science, Vol. 17, pages 721–735 (1973).

Illustrative examples of the difunctional agents useful in this invention are polyhaloalkanols such as 1,3-dichloroisopropanol; 1,3-dibromoisopropanol; sulfonium zwitterions such as the tetrahydrothiophene adduct of novolac resins; haloepoxyalkanes such as epichlorohydrin, epibromohydrin, 2-methyl epichlorohydrin and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers having an epoxy equivalent weight range from about 175 to about 380, bisphenol A-epichlorohydrin epoxy resins having an epoxy equivalent weight range from about 182 to about 975 and mixtures of the foregoing.

Also useful as crosslinking agents are monomeric amine-epihalohydrin adducts prepared by reacting at least two moles of an epihalohydrin with one mole of various monoamines, diamines and triamines at a temperature in the range from 0° to 90° C. for a time period of 0.5 to 8 hours. The reaction is carried out in a reaction media containing 20 to 90 percent water, lower alcohols such as methanol or ethanol, or in aqueous solutions of the lower alcohols. The amine-epihalohydrin adducts are used directly as made without separation or concentration. The preparation and use of monomeric amine-epihalohydrin adducts as crosslinking agents is further disclosed in the patent application by J. R. Gross, U.S. Pat. No. 4,310,593 (1-12-82). This patent is incorporated by reference herein.

Sulfonium zwitterions are known from U.S. Pat. Nos. 3,660,431, 3,749,737, and 3,749,738. The disclosures of these patents are incorporated herein by reference.

These crosslinking agents are used in an amount from about 0.05 to about 5.0% based on the weight of the polyelectrolyte used. This is generally sufficient to cause the polyelectrolyte to become lightly crosslinked.

It is sometimes desirable to add a small amount of an surfactant to the polyelectrolyte composition to aid in flowing on and removing the continuous film from the water impervious substrate. A secondary benefit of using a surfactant is to increase the wettability of the final dry absorbent film. Either anionic or nonionic surfactants may be used. Examples of the useful surfactants are the sodium alkyl sulfonates and the ethylene oxide derivatives of alkylated phenols and the like.

For the purpose of this invention, a moisture absorbent or water swellable polyelectrolyte or polymer is defined as one which absorbs greater than about 9 times its weight of synthetic or natural urine. Preferably the absorbency should be in the range from about 15–60 grams of urine per gram of polyelectrolyte or in the range of 90–250 grams of deionized water per gram of polyelectrolyte. The level of crosslinking agent used is a variable factor which is dependent upon the particular polyelectrolyte used and the molecular weight of the polyelectrolyte. Preferrably, the amount used varies from the 0.25 to 3.0 percent based on the weight of the polyelectrolyte. However, this range is varied for each polyelectrolyte in order to adjust the absorbency of the final crosslinked material.

The water-swellable composites of this invention may be combined into absorbent pads with wicking or non-wicking substrates. Examples of wicking substrates include woven fabrics, non-woven fiber mats, cellulose fluff, polymeric foams, tissue paper, crepe paper, paper wadding, and paper toweling.

The soft hand composites of this invention are made by first reducing if necessary the moisture content of the composites. It is to be understood that similar soft composites can be made using the film laminates of U.S. Pat. No. 4,076,673 or 4,117,184, and similar laminates wherein the polymer is in the form of fibers or powders.

The moisture content of the composites must be reduced from their normal content of about 14% moisture to less than 8% and preferably in the range from 1–6%. If the moisture content is greater than about 8%, there is substantially no fracturing or breaking of the absorbent layer in the subsequent creping zone since the polymer remains flexible.

The above drying step can be accomplished with conventional drying equipment such as a steam heated drying drum, microwave heaters, infrared heaters, hot forced air, or similar equipment.

The second step of the process involves passing the dry composite through a creping zone wherein the absorbent polymer layer is fractured or broken but which remains substantially bonded to the substrates. This can be accomplished by passing the dried composite through a conventional dry creping machine.

The following examples are presented to further illustrate but not limit the invention.

EXAMPLES 1–4

A 7.5-inch wide roll of tissue paper/aerated film/tissue paper composite was prepared according to U.S. Pat. No. 4,117,184 and had the following characteristics: total weight 7.1 grams per square feet; paper tissue weight 1.37 grams/ft.$^2$; film weight 3.8 grams/ft$^2$; film moisture content 14 percent.

The composite was unwound from the feed roll and dried to a moisture content of 5 percent in an oven equipped with infra red light bulbs.

Various lengths of this dried roll were then microcreped with varying degrees of creping in a machine such as disclosed in U.S. Pat. No. 3,260,778. Samples were then evaluated for their softness or hand on a Handle-O-Meter, capacity for absorbing 1% aqueous sodium chloride, and rate of liquid absorption. The samples were tested for their absorption rate by the following test:

A sample of the laminate on a glass plate was placed under a 6 by 6 inch square metal box having ¼ inch thick walls. The box was weighted with lead weights on each corner to prevent leakage. Since the capacity of film to absorb water in the laminate (grams of saline solution per gram of film) and the weight of the film per square foot is known, it can be calculated what the capacity of the laminate sample will be. The saline solution used is 1% sodium chloride in water to simulate urine.

Into this box is poured 75% of the known capacity of the 36 inch square sample and a timer is started. When the liquid is absorbed completely as shown by lack of gloss due to free liquid, the timer is stopped. The time in seconds is the absorption rate.

The samples were tested for their capacity to absorb sodium chloride solutions (synthetic urine) by the following test:

A 4-inch by 5-inch piece of the laminate was added to a 250 ml beaker containing 150 grams of a 1% aqueous sodium chloride solution. The solution was stirred for 3 minutes using a magnetic stirring bar so that the sample was broken up.

The contents of the beaker was poured on to a filter screen and the liquid was collected in a tared container for 17 minutes. The filtrate was weighed and the capacity was found by the expression $$\frac{(\text{sample weight in gms/ft}^2) \times (150 \text{ weight of filtrate})}{\text{dry sample weight in gms.}} = $$

capacity in grams/ft$^2$.

The Handle-O-Meter is a standard testing machine for softness in the paper and clothing industries wherein a lower number denotes softness. The meter used herein was the 211-5 model sold by the Thwing-Albert Instrument Company of Philadelphia, PA. The results are shown in Table I.

Example 1 was given a rough crepe of about 30–50% reduction in length.

Example 2 was given a fine crepe of about 30–50% reduction in length followed by a stretching operation leaving a 5% reduction in length and a non-woven cushion was used between the grooved roll of the microcreper and the absorbent composite to prevent scuffing and tearing of the laminate.

Example 3 was given the same treatment as in Example 2 except that Example 3 was given a stretch resulting in a 20% reduction in length.

Example 4 was given the same treatment as in Example 3 except that Example 4 was given a stretch resulting in a 10–15% reduction in length.

Control A was a tissue paper/film/tissue paper composite prepared according to U.S. Pat. No. 4,117,184 and given a needle punch operation wherein 0.090-inch diameter needles were punched through the laminate in a grid pattern 0.250 inches apart.

Control B was the same as Control A but was not needle punched.

TABLE I

| Runs | Softness CD | Softness MD | Weight in gms/sq. ft | Capacity in gms/sq. ft | Absorption rate in seconds |
|---|---|---|---|---|---|
| Ex. 1 | 17 | >125 | 9.7 | 261 | 38 |
| Ex. 2 | 22.2 | " | 7.8 | 218 | 42 |
| Ex. 3 | 29.3 | " | 7.9 | 217 | 45 |
| Ex. 4 | 22 | " | 7.8 | 213 | 57 |
| Control B | >125 | " | 7.1 | 190 | >100 |
| Control A | 107 | 110 | 6.57 | 193 | 65 |

MD = machine direction.
CD = cross direction.

EXAMPLES 5-9

Samples were prepared and tested as in Examples 1-4, dried to below 5% moisture, and microcreped. The results are given in Table II.

Example 5 was given a coarse crepe (of 30–50% reduction in length) followed by a stretch resulting in a final reduction of 8% in length.

Example 6 was given a medium crepe (30–50% reduction in length) and no stretch, resulting in a final reduction in length of 30–50%.

Example 7 was given a medium crepe (30–50% reduction) followed by a stretch resulting in a final reduction in length of 6%.

Example 8 was given a medium crepe (30–50% reduction) followed by a stretch resulting in a final reduction of 5% in length.

Example 9 was given a medium crepe (30–50% reduction) followed by a stretch resulting in a final reduction of 10% in length.

As controls to show the importance of the drying step, the following control runs were made using the same laminate of Examples 5–9 but not dried to below 5% moisture content.

Control 1 was given a fine crepe 30–50% reduction with no stretching.

Control 2 was given a fine crepe with a stretch resulting in a final length reduction of 5%.

Control 3 was given a coarse crepe with a stretch resulting in a final reduction in length of about 5%.

Control 4 was given a coarse crepe with a stretch resulting in a final reduction in length of about 15%.

Control 5 was given a fine crepe with a stretch resulting in a final reduction in length of about 15%.

Control 6 was given a fine crepe with a stretch resulting in a final reduction in length of about 9%.

As further controls to illustrate the importance of the dry creping step the following control was also run.

Control 7 was merely dried reducing the moisture content below 5% but it was not microcreped.

TABLE II

| Runs | Softness CD | Softness MD | Softness Average | Weight gms/sq. ft | Capacity gms/sq. ft | Absorption rate in seconds |
|---|---|---|---|---|---|---|
| Ex. 5 | 124 | 27 | 75 | 7.3 | 182 | 43 |
| Ex. 6 | 129 | 19 | 74 | 9.6 | 255 | 37 |
| Ex. 7 | 124 | 26 | 75 | 7.8 | 214 | 31 |
| Ex. 8 | 78 | 22 | 50 | 7.6 | 213 | 36 |
| Ex. 9 | 82 | 22 | 52 | 8.1 | 214 | 30 |
| Control 1 | >136 | 149 | >142 | 13.1 | 384 | 300 |
| Control 2 | >128 | 130 | >129 | 7.2 | 202 | 380 |

TABLE II-continued

| Runs | Softness CD | Softness MD | Softness Average | Weight gms/ sq. ft | Capacity gms/ sq. ft | Absorption rate in seconds |
|---|---|---|---|---|---|---|
| Control 3 | >128 | 114 | 121 | 7.0 | 198 | 290 |
| Control 4 | >129 | 118 | 124 | 7.4 | 207 | 250 |
| Control 5 | >128 | 112 | 120 | 7.8 | 244 | 340 |
| Control 6 | >138 | 118 | 128 | 7.4 | 205 | 350 |
| Control 7 | 126 | 122 | 124 | 7.3 | 198 | 230 |

The data in Table II show that the drying step is necessary to achieve a superior absorption rate for creped composites having about the same absorptive capacity.

EXAMPLE 10

A non-wet strength tissue paper weighing 10 lbs/3000 ft² was cut approximately 1 foot wide by 2 feet long and placed on a laboratory table. A light mist of water was sprayed on the surface of the tissue and immediately a polymeric absorbent powder was sprinkled on the wet tissue surface. The absorbent powder was made by chopping up an absorbent film made by the method disclosed in U.S. Pat. No. 4,117,184 in a Waring blendor. A light mist of water was then sprayed on the surface of the absorbent powder and a second tissue sheet placed on the surface and pressed on the powder surface using a lightweight hand roller. The composite structure was rolled into a roll and aged in a constant humidity/temperature room for 24 hours.

After 24 hours aging the sample composite was removed, and dried to a moisture content of about 2-3 percent. At this moisture content, the composite was quite stiff.

The composite was then folded in about ⅛ inch folds in the machine direction and then stretched so that a one foot long sample was about 8 inches long. An 8-inch × 8-inch sample was cut and placed in a controlled humidity room at 20 percent relative humidity and 70° F. for 24 hours. The sample was tested on the Handle-O-Meter and found to be soft in the CD direction giving a reading of 30 and stiff in the MD direction showing a reading of >125. This example shows that a composite, wherein a powder form of polymeric absorbent is the center layer of the composite, can be softened similar to the effect achieved when the polymer layer is a film.

EXAMPLE 11

In a similar manner, a composite can be made from the same tissue paper of Example 10 using the same procedure and substituting an absorbent fiber for the absorbent powder.

I claim:

1. A creped hydrophilic absorbent composite which has a rapid absorption rate and has a soft hand at low relative humidities which comprises the product produced by
   (a) reducing the moisture content of a composite of a water-swellable hydrophilic polymer with wicking substrates to less than 8% by weight by passing said composite through a drying zone, and
   (b) passing said dried composite through a creping zone wherein said polymer is fractured and broken into pieces which remain essentially laminated to said substrates.

2. The composite as set forth in claim 1 wherein the hydrophilic composite before being creped comprises a composite of a wicking substrate bonded to a hydrophilic polymer wherein the polymer is in a form selected from the group consisting of a film, a random fiber mat, and a powder.

3. The composite of claim 2 wherein said polymer comprises an aerated film having a density ranging from about 1.1 to 0.3 grams per cubic centimeter.

4. The composite of claim 1 wherein said wicking substrate is selected from the group consisting of woven fabrics, paper tissues non-woven fiber mats and polymeric foams.

5. An absorbent pad which comprises the absorbent composite of claim 1, one or more layers of wicking substrates, a water impermeable bottom sheet and a water permeable face sheet.

6. The absorbent pad of claim 5 wherein said water impermeable bottom sheet is polyethylene and said face sheet is a non-woven fiber mat.

7. A process for making the creped composite of claim 1 which comprises
   (a) reducing the moisture content of a composite of a water-swellable hydrophilic polymer with wicking substrates to less than 8% by weight by passing said composite through a drying zone, and
   (b) passing said dried composite through a creping zone wherein said polymer breaks into a plurality of pieces which remain essentially laminated to said substrates.

8. The process of claim 7 wherein said composite has a moisture content in the range from 1 to 6%.

9. The process of claim 7 wherein the water-swellable hydrophilic polymer is a lightly crosslinked carboxylic polyelectrolyte.

10. The process of claim 7 wherein the water-swellable hydrophilic polymer is in the form of a film.

11. The process of claim 10 wherein the film comprises an aerated film having a density ranging from about 1.1 to 0.3 grams per cubic centimeter.

12. A creped hydrophilic absorbent composite which has a rapid absorption rate and has a soft hand at low relative humidities which comprises the product produced by
   (a) reducing the moisture content of a composite of a lightly crosslinked carboxylic polyelectrolyte with wicking substrates to less than 8% by weight by passing said composite through a drying zone, and
   (b) passing said dried composite through a creping zone wherein said polyelectrolyte is fractured and broken into pieces which remain essentially laminated to said substrates.

13. The composite as set forth in claim 1 wherein the hydrophilic composite before being creped comprises a composite of a wicking substrate bonded to a lightly crosslinked carboxylic polyelectrolyte wherein the polyelectrolyte is in a form selected from the group consisting of a film, a random fiber mat, and a powder.

14. The composite of claim 13 wherein the film comprises an aerated film having a density ranging from about 1.1 to 0.3 grams per cubic centimeter.

15. The composite of claim 12 wherein said wicking substrate is selected from the group consisting of woven fabrics, paper tissues non-woven fiber mats and polymeric foams.

16. An absorbent pad which comprises the absorbent composite of claim 12, one or more layers of wicking substrates, a water impermeable bottom sheet and a water permeable face sheet.

17. The absorbent pad of claim 16 wherein said water impermeable bottom sheet is polyethylene and said face sheet is a non-woven fiber mat.

* * * * *

UNITED STATES PATENT AND TRADEMARK OFFICE
CERTIFICATE OF CORRECTION

PATENT NO. : 4,500,585

DATED : February 19, 1985

INVENTOR(S) : Robert E. Erickson

It is certified that error appears in the above-identified patent and that said Letters Patent is hereby corrected as shown below:

Col. 5, line 37; "150 weight of filtrate" should read --150-weight of filtrate--.

Signed and Sealed this

Seventeenth Day of September 1985

[SEAL]

Attest:

DONALD J. QUIGG

Attesting Officer

Commissioner of Patents and Trademarks—Designate